(12) United States Patent
Voltenburg, Jr. et al.

(10) Patent No.: US 8,062,008 B2
(45) Date of Patent: Nov. 22, 2011

(54) PERISTALTIC PUMP AND REMOVABLE CASSETTE THEREFOR

(75) Inventors: Robert R. Voltenburg, Jr., Davison, MI (US); Loren M. Thompson, Lapeer, MI (US)

(73) Assignee: Curlin Medical Inc., East Aurora, NY (US)

( * ) Notice: Subject to any disclaimer, the term of this patent is extended or adjusted under 35 U.S.C. 154(b) by 1090 days.

(21) Appl. No.: 11/862,360

(22) Filed: Sep. 27, 2007

(65) Prior Publication Data

US 2009/0087327 A1 Apr. 2, 2009

(51) Int. Cl.
*F04B 43/08* (2006.01)
*F04B 43/12* (2006.01)
*F04B 45/06* (2006.01)

(52) U.S. Cl. ...................... 417/477.2; 604/250
(58) Field of Classification Search ............... 417/477.2, 417/474, 477.1; 604/153, 246, 250
See application file for complete search history.

(56) References Cited

U.S. PATENT DOCUMENTS

| | | | |
|---|---|---|---|
| 3,921,622 A | 11/1975 | Cole | |
| 3,963,023 A | 6/1976 | Hankinson | |
| 4,178,138 A | 12/1979 | Iles | |
| 4,187,057 A | 2/1980 | Xanthopoulos | |
| 4,256,437 A | 3/1981 | Brown | |
| 4,418,565 A | 12/1983 | St. John | |
| 4,460,358 A | 7/1984 | Somerville et al. | |
| 4,537,561 A | 8/1985 | Xanthopoulos | |
| 4,565,500 A | 1/1986 | Jeensalute et al. | |
| 4,586,691 A | 5/1986 | Kozlow | |
| 4,599,055 A | 7/1986 | Dykstra | |
| 4,673,334 A | 6/1987 | Allington et al. | |
| 4,689,043 A | 8/1987 | Bisha | |
| 4,722,224 A | 2/1988 | Scheller et al. | |
| 4,735,558 A | 4/1988 | Kienholz et al. | |
| 4,764,116 A | 8/1988 | Shoher et al. | |
| 4,764,166 A | 8/1988 | Spani | |
| 4,798,580 A | 1/1989 | DeMeo et al. | |
| 4,821,558 A | 4/1989 | Pastrone et al. | |
| 4,846,792 A | 7/1989 | Bobo, Jr. et al. | |
| 4,863,425 A | 9/1989 | Slate et al. | |
| 4,865,584 A | 9/1989 | Epstein et al. | |
| 4,884,013 A | 11/1989 | Jackson et al. | |

(Continued)

FOREIGN PATENT DOCUMENTS

CA 2479707 3/2005

(Continued)

OTHER PUBLICATIONS

The International Bureau of WIPO, International Preliminary Report on Patentability in International Application No. PCT/US2008/011130, issued Mar. 30, 2010.
U.S. Appl. No. 11/862,302, filed Sep. 27, 2007, Voltenburg et al.
U.S. Appl. No. 11/862,326, filed Sep. 27, 2007, Voltenburg et al.
International Search Report dated Dec. 2, 2008.

*Primary Examiner* — Devon C Kramer
*Assistant Examiner* — Peter J Bertheaud
(74) *Attorney, Agent, or Firm* — Hodgson Russ LLP

(57) ABSTRACT

A removable cassette for a peristaltic pump includes a cassette body and an occluder disposed at least partially in the cassette body and configured to be movable between an occluding position and a non-occluding position. The occluder includes an occluder body and an anti-ejection member integrally formed on the occluder body. The anti-ejection member is configured to substantially prevent the removal of the cassette from the peristaltic pump when the occluder is in the non-occluding position.

20 Claims, 4 Drawing Sheets

U.S. PATENT DOCUMENTS

| | | | |
|---|---|---|---|
| 4,886,431 A | 12/1989 | Soderquist et al. | |
| 4,909,713 A | 3/1990 | Finsterwald et al. | |
| 4,943,279 A | 7/1990 | Samiotes et al. | |
| 4,944,191 A | 7/1990 | Pastrone et al. | |
| 4,950,235 A | 8/1990 | Slate et al. | |
| 4,950,245 A | 8/1990 | Brown et al. | |
| 4,978,335 A | 12/1990 | Arthur, III | |
| 4,979,940 A | 12/1990 | Bobo, Jr. et al. | |
| 4,981,467 A | 1/1991 | Bobo, Jr. et al. | |
| 5,000,663 A | 3/1991 | Gorton | |
| 5,006,110 A | 4/1991 | Garrison et al. | |
| 5,011,378 A | 4/1991 | Brown et al. | |
| 5,041,086 A | 8/1991 | Koenig et al. | |
| 5,053,747 A | 10/1991 | Slate et al. | |
| 5,059,171 A | 10/1991 | Bridge et al. | |
| 5,064,412 A | 11/1991 | Henke et al. | |
| 5,078,683 A | 1/1992 | Sancoff et al. | |
| 5,096,385 A | 3/1992 | Georgi et al. | |
| 5,098,380 A | 3/1992 | Aizawa et al. | |
| 5,102,392 A | 4/1992 | Sakai et al. | |
| 5,106,366 A | 4/1992 | Steppe | |
| 5,116,203 A | 5/1992 | Natwick et al. | |
| 5,125,891 A | 6/1992 | Hossain et al. | |
| 5,126,616 A | 6/1992 | Gorton et al. | |
| 5,163,900 A | 11/1992 | Wortrich | |
| 5,176,631 A | 1/1993 | Koenig | |
| 5,177,993 A | 1/1993 | Beckman et al. | |
| 5,181,910 A | 1/1993 | Scanlon | |
| 5,191,795 A | 3/1993 | Fellingham et al. | |
| 5,195,960 A | 3/1993 | Hossain et al. | |
| 5,213,483 A | 5/1993 | Flaherty et al. | |
| 5,219,330 A | 6/1993 | Bollish et al. | |
| 5,242,408 A | 9/1993 | Jhuboo et al. | |
| 5,256,156 A | 10/1993 | Kern et al. | |
| 5,256,157 A | 10/1993 | Samiotes et al. | |
| 5,257,917 A | 11/1993 | Minarik et al. | |
| 5,267,956 A | 12/1993 | Beuchat | |
| 5,282,787 A | 2/1994 | Wortrich | |
| 5,292,306 A | 3/1994 | Wynkoop et al. | |
| 5,300,044 A | 4/1994 | Classey et al. | |
| 5,317,506 A | 5/1994 | Coutre et al. | |
| 5,328,460 A | 7/1994 | Lord et al. | |
| 5,337,747 A | 8/1994 | Neftel | |
| 5,338,157 A | 8/1994 | Blomquist | |
| 5,356,378 A | 10/1994 | Doan | |
| 5,380,173 A | 1/1995 | Hellstrom | |
| 5,387,088 A | 2/1995 | Knapp et al. | |
| 5,394,732 A | 3/1995 | Johnson et al. | |
| 5,395,320 A | 3/1995 | Padda et al. | |
| 5,397,222 A | 3/1995 | Moss et al. | |
| 5,427,509 A | 6/1995 | Chapman et al. | |
| 5,429,602 A | 7/1995 | Hauser | |
| 5,433,588 A | 7/1995 | Monk et al. | |
| 5,437,635 A | 8/1995 | Fields et al. | |
| 5,445,506 A | 8/1995 | Afflerbaugh et al. | |
| 5,447,417 A | 9/1995 | Kuhl et al. | |
| 5,453,098 A | 9/1995 | Botts et al. | |
| 5,462,416 A | 10/1995 | Dennehey et al. | |
| 5,480,294 A | 1/1996 | Di Perna et al. | |
| 5,480,386 A | 1/1996 | Brohy et al. | |
| 5,482,438 A | 1/1996 | Anderson et al. | |
| 5,482,446 A | 1/1996 | Williamson et al. | |
| 5,485,408 A | 1/1996 | Blomquist | |
| 5,501,665 A | 3/1996 | Jhuboo et al. | |
| 5,514,102 A | 5/1996 | Winterer et al. | |
| 5,515,713 A | 5/1996 | Saugues et al. | |
| 5,518,378 A | 5/1996 | Neftel et al. | |
| 5,537,853 A | 7/1996 | Finburgh et al. | |
| 5,538,405 A | 7/1996 | Patno et al. | |
| D376,848 S | 12/1996 | Zeilig et al. | |
| 5,588,815 A | 12/1996 | Zaleski, II | |
| 5,601,420 A | 2/1997 | Warner et al. | |
| 5,609,575 A | 3/1997 | Larson et al. | |
| 5,620,312 A | 4/1997 | Hyman et al. | |
| 5,626,563 A | 5/1997 | Dodge et al. | |
| 5,628,619 A | 5/1997 | Wilson | |
| D380,260 S | 6/1997 | Hyman | |
| 5,637,093 A | 6/1997 | Hyman et al. | |
| 5,646,727 A | 7/1997 | Hammer et al. | |
| 5,647,853 A | 7/1997 | Feldmann et al. | |
| 5,655,897 A | 8/1997 | Neftel et al. | |
| 5,657,000 A | 8/1997 | Ellingboe | |
| 5,658,250 A | 8/1997 | Blomquist et al. | |
| 5,669,877 A | 9/1997 | Blomquist | |
| 5,676,530 A | 10/1997 | Nazarifar | |
| 5,680,111 A | 10/1997 | Danby et al. | |
| 5,681,285 A | 10/1997 | Ford et al. | |
| 5,683,367 A | 11/1997 | Jordan et al. | |
| 5,685,844 A | 11/1997 | Marttila | |
| 5,695,473 A | 12/1997 | Olsen | |
| 5,709,539 A | 1/1998 | Hammer et al. | |
| 5,713,856 A | 2/1998 | Eggers et al. | |
| 5,718,568 A | 2/1998 | Neftel et al. | |
| 5,720,721 A | 2/1998 | Dumas et al. | |
| 5,741,125 A | 4/1998 | Neftel et al. | |
| 5,752,813 A | 5/1998 | Tyner et al. | |
| 5,755,691 A | 5/1998 | Hilborne | |
| 5,759,015 A | 6/1998 | Van Lintel et al. | |
| 5,764,159 A | 6/1998 | Neftel | |
| 5,766,155 A | 6/1998 | Hyman et al. | |
| 5,772,635 A | 6/1998 | Dastur et al. | |
| 5,782,611 A | 7/1998 | Neftel et al. | |
| 5,782,805 A | 7/1998 | Meinzer et al. | |
| 5,788,669 A | 8/1998 | Peterson | |
| 5,791,880 A | 8/1998 | Wilson | |
| 5,795,317 A | 8/1998 | Brierton et al. | |
| 5,795,327 A | 8/1998 | Wilson et al. | |
| 5,800,387 A | 9/1998 | Duffy et al. | |
| 5,811,659 A | 9/1998 | Giebler | |
| 5,827,223 A | 10/1998 | Butterfield | |
| 5,827,262 A | 10/1998 | Neftel et al. | |
| 5,836,910 A | 11/1998 | Duffy et al. | |
| 5,840,068 A | 11/1998 | Cartledge et al. | |
| 5,842,841 A | 12/1998 | Danby et al. | |
| 5,843,035 A | 12/1998 | Bowman et al. | |
| 5,848,988 A | 12/1998 | Davis | |
| 5,853,386 A | 12/1998 | Davis et al. | |
| 5,853,398 A | 12/1998 | Lal et al. | |
| 5,897,524 A | 4/1999 | Wortrich et al. | |
| 5,904,668 A | 5/1999 | Hyman et al. | |
| 5,906,589 A | 5/1999 | Gordon et al. | |
| 5,927,956 A | 7/1999 | Lim et al. | |
| 5,928,196 A | 7/1999 | Johnson et al. | |
| 5,935,099 A | 8/1999 | Peterson et al. | |
| 5,935,106 A | 8/1999 | Olsen | |
| 5,938,413 A | 8/1999 | Makino et al. | |
| 5,941,846 A | 8/1999 | Duffy et al. | |
| 5,954,485 A | 9/1999 | Johnson et al. | |
| 5,961,487 A | 10/1999 | Davis | |
| 5,967,484 A | 10/1999 | Morris | |
| 5,968,014 A | 10/1999 | Neftel et al. | |
| 5,984,894 A | 11/1999 | Poulsen et al. | |
| 5,989,222 A | 11/1999 | Cole et al. | |
| 5,993,420 A | 11/1999 | Hyman et al. | |
| 6,013,057 A | 1/2000 | Danby et al. | |
| 6,059,765 A | 5/2000 | Cole et al. | |
| 6,068,612 A | 5/2000 | Bowman et al. | |
| 6,077,055 A | 6/2000 | Vilks | |
| 6,077,246 A | 6/2000 | Kullas et al. | |
| 6,085,574 A | 7/2000 | Neftel et al. | |
| 6,106,498 A | 8/2000 | Friedli et al. | |
| 6,109,895 A | 8/2000 | Ray et al. | |
| 6,110,153 A | 8/2000 | Davis et al. | |
| 6,120,490 A | 9/2000 | Neftel | |
| 6,123,524 A | 9/2000 | Danby et al. | |
| 6,129,517 A | 10/2000 | Danby et al. | |
| 6,129,699 A | 10/2000 | Haight et al. | |
| 6,142,008 A | 11/2000 | Cole et al. | |
| 6,146,109 A | 11/2000 | Davis et al. | |
| 6,195,887 B1 | 3/2001 | Danby et al. | |
| 6,203,296 B1 | 3/2001 | Ray et al. | |
| 6,203,528 B1 | 3/2001 | Deckert et al. | |
| 6,212,936 B1 | 4/2001 | Meisberger | |
| 6,213,723 B1 | 4/2001 | Danby et al. | |
| 6,213,738 B1 | 4/2001 | Danby et al. | |
| 6,231,320 B1 | 5/2001 | Lawless et al. | |
| 6,234,992 B1 | 5/2001 | Haight et al. | |

| | | |
|---|---|---|
| 6,241,704 B1 | 6/2001 | Peterson et al. |
| 6,248,067 B1 | 6/2001 | Causey, III et al. |
| 6,261,262 B1 * | 7/2001 | Briggs et al. .............. 604/153 |
| 6,269,340 B1 | 7/2001 | Ford et al. |
| D446,854 S | 8/2001 | Cheney, II et al. |
| 6,270,673 B1 | 8/2001 | Belt et al. |
| 6,280,430 B1 | 8/2001 | Neftel et al. |
| 6,293,926 B1 | 9/2001 | Sorensen et al. |
| 6,328,712 B1 | 12/2001 | Cartledge et al. |
| 6,358,225 B1 | 3/2002 | Butterfield |
| 6,362,591 B1 | 3/2002 | Moberg |
| 6,364,279 B1 | 4/2002 | Neftel et al. |
| 6,423,029 B1 | 7/2002 | Elsberry |
| 6,447,481 B1 | 9/2002 | Duchon et al. |
| 6,468,059 B2 | 10/2002 | Haser et al. |
| 6,475,180 B2 | 11/2002 | Peterson et al. |
| 6,489,896 B1 | 12/2002 | Platt et al. |
| 6,519,569 B1 | 2/2003 | White et al. |
| 6,539,250 B1 | 3/2003 | Bettinger |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,558,343 B1 | 5/2003 | Neftel |
| 6,572,349 B2 | 6/2003 | Sorensen et al. |
| 6,572,604 B1 | 6/2003 | Platt et al. |
| 6,629,955 B2 * | 10/2003 | Morris et al. .............. 604/153 |
| 6,632,190 B2 | 10/2003 | Simonini et al. |
| 6,635,033 B1 | 10/2003 | Hill et al. |
| 6,641,533 B2 | 11/2003 | Causey, III et al. |
| 6,648,861 B2 | 11/2003 | Platt et al. |
| 6,670,885 B2 | 12/2003 | Kosaka |
| 6,689,091 B2 | 2/2004 | Bui et al. |
| 6,716,193 B1 | 4/2004 | Neftel |
| 6,731,216 B2 | 5/2004 | Ho et al. |
| 6,742,992 B2 | 6/2004 | Davis |
| 6,790,198 B1 | 9/2004 | White et al. |
| 6,809,653 B1 | 10/2004 | Mann et al. |
| 6,835,049 B2 | 12/2004 | Ray |
| 6,852,104 B2 | 2/2005 | Blomquist |
| 6,872,200 B2 | 3/2005 | Mann et al. |
| 6,889,556 B2 | 5/2005 | Steger |
| 6,936,029 B2 | 8/2005 | Mann et al. |
| 6,942,473 B2 * | 9/2005 | Abrahamson et al. ........ 417/474 |
| 6,942,637 B2 | 9/2005 | Cartledge et al. |
| 6,962,488 B2 | 11/2005 | Davis et al. |
| 6,966,895 B2 | 11/2005 | Tribe |
| 6,979,326 B2 | 12/2005 | Mann et al. |
| 6,985,870 B2 | 1/2006 | Martucci et al. |
| 6,997,905 B2 | 2/2006 | Gillespie, Jr. et al. |
| 6,997,920 B2 | 2/2006 | Mann et al. |
| 6,999,854 B2 | 2/2006 | Roth |
| 7,001,153 B2 | 2/2006 | McDowell et al. |
| 7,018,182 B2 | 3/2006 | O'Mahony et al. |
| 7,025,743 B2 | 4/2006 | Mann et al. |
| 7,048,193 B2 | 5/2006 | Tsukada et al. |
| 7,070,578 B2 | 7/2006 | Leukanech et al. |
| 7,074,205 B1 | 7/2006 | Duffy et al. |
| 7,098,803 B2 | 8/2006 | Mann et al. |
| 7,109,878 B2 | 9/2006 | Mann et al. |
| 7,117,041 B2 | 10/2006 | Engleson et al. |
| 7,141,037 B2 | 11/2006 | Butterfield et al. |
| 7,150,735 B2 | 12/2006 | Hickle |
| 7,160,284 B2 | 1/2007 | Ullestad et al. |
| 7,193,521 B2 | 3/2007 | Moberg et al. |
| 7,195,607 B2 | 3/2007 | Westberg et al. |
| 7,204,823 B2 | 4/2007 | Estes et al. |
| 7,214,038 B2 | 5/2007 | Saxer et al. |
| 7,223,079 B2 | 5/2007 | Ortega et al. |
| 7,236,936 B2 | 6/2007 | White et al. |
| 7,239,941 B2 | 7/2007 | Mori et al. |
| 7,264,148 B2 | 9/2007 | Tachibana |
| 7,311,691 B2 | 12/2007 | Cartledge et al. |
| 2001/0004444 A1 | 6/2001 | Haser et al. |
| 2001/0049608 A1 | 12/2001 | Hochman |
| 2002/0002326 A1 | 1/2002 | Causey, III et al. |
| 2002/0016570 A1 | 2/2002 | Cartledge et al. |
| 2002/0029776 A1 | 3/2002 | Blomquist |
| 2002/0077852 A1 | 6/2002 | Ford et al. |
| 2002/0077856 A1 | 6/2002 | Pawlikowski et al. |
| 2002/0099334 A1 | 7/2002 | Hanson et al. |
| 2002/0104370 A1 | 8/2002 | Steger et al. |
| 2002/0138155 A1 | 9/2002 | Bristol |
| 2002/0169636 A1 | 11/2002 | Eggers et al. |
| 2002/0183693 A1 | 12/2002 | Peterson et al. |
| 2002/0193679 A1 | 12/2002 | Malave et al. |
| 2003/0004458 A1 | 1/2003 | Platt et al. |
| 2003/0060765 A1 | 3/2003 | Campbell et al. |
| 2003/0106553 A1 | 6/2003 | Vanderveen |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0212364 A1 | 11/2003 | Mann et al. |
| 2003/0222548 A1 | 12/2003 | Richardson et al. |
| 2004/0010425 A1 | 1/2004 | Wilkes et al. |
| 2004/0019464 A1 | 1/2004 | Martucci et al. |
| 2004/0019607 A1 | 1/2004 | Moubayed et al. |
| 2004/0057856 A1 | 3/2004 | Saxer et al. |
| 2004/0064435 A1 | 4/2004 | Moubayed et al. |
| 2004/0073095 A1 | 4/2004 | Causey, III et al. |
| 2004/0078231 A1 | 4/2004 | Wilkes et al. |
| 2004/0103897 A1 | 6/2004 | Hickle et al. |
| 2004/0107965 A1 | 6/2004 | Hickle et al. |
| 2004/0116862 A1 | 6/2004 | Ray |
| 2004/0121767 A1 | 6/2004 | Simpson et al. |
| 2004/0158193 A1 | 8/2004 | Bui et al. |
| 2004/0167465 A1 | 8/2004 | Mihai et al. |
| 2004/0167495 A1 | 8/2004 | Neftel |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176984 A1 | 9/2004 | White et al. |
| 2004/0193325 A1 | 9/2004 | Bonderud et al. |
| 2004/0225252 A1 | 11/2004 | Gillespie, Jr. et al. |
| 2005/0020978 A1 | 1/2005 | Vollenweider |
| 2005/0021006 A1 | 1/2005 | Tonnies |
| 2005/0021368 A1 | 1/2005 | Burkeen et al. |
| 2005/0022274 A1 | 1/2005 | Campbell et al. |
| 2005/0029277 A1 | 2/2005 | Tachibana |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0069437 A1 | 3/2005 | Mittelstein et al. |
| 2005/0089994 A1 | 4/2005 | Neftel |
| 2005/0095152 A1 | 5/2005 | Dale |
| 2005/0096593 A1 | 5/2005 | Pope et al. |
| 2005/0101907 A1 | 5/2005 | Sondeen et al. |
| 2005/0118048 A1 | 6/2005 | Traxinger |
| 2005/0124929 A1 | 6/2005 | Katz et al. |
| 2005/0137530 A1 | 6/2005 | Campbell et al. |
| 2005/0137653 A1 | 6/2005 | Friedman et al. |
| 2005/0139651 A1 | 6/2005 | Lim et al. |
| 2005/0143864 A1 | 6/2005 | Blomquist |
| 2005/0148869 A1 | 7/2005 | Masuda |
| 2005/0154368 A1 | 7/2005 | Lim et al. |
| 2005/0171513 A1 | 8/2005 | Mann et al. |
| 2005/0177395 A1 | 8/2005 | Blomquist |
| 2005/0182366 A1 | 8/2005 | Vogt et al. |
| 2005/0196307 A1 | 9/2005 | Limoges |
| 2005/0214129 A1 | 9/2005 | Greene et al. |
| 2005/0234382 A1 | 10/2005 | Tonelli et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |

| | | | | | |
|---|---|---|---|---|---|
| 2005/0278073 A1 | 12/2005 | Roth | DE | 102 44 090 | 4/2004 |
| 2005/0283210 A1 | 12/2005 | Blischak et al. | DE | 10359735 | 7/2005 |
| 2006/0001550 A1 | 1/2006 | Mann et al. | EP | 164020 | 12/1985 |
| 2006/0002799 A1 | 1/2006 | Schann et al. | EP | 0 293 081 A1 | 11/1988 |
| 2006/0002805 A1 | 1/2006 | Schann et al. | EP | 0 293 591 A2 | 12/1988 |
| 2006/0007017 A1 | 1/2006 | Mann et al. | EP | 0 036 130 A1 | 3/1989 |
| 2006/0009734 A1 | 1/2006 | Martin | EP | 0 319 275 A1 | 6/1989 |
| 2006/0027523 A1 | 2/2006 | Van Lintel et al. | EP | 0 327 209 A2 | 8/1989 |
| 2006/0058804 A1 | 3/2006 | Mollstam | EP | 0 332 330 | 9/1989 |
| 2006/0100746 A1 | 5/2006 | Leibner-Druska | EP | 0 335 385 A2 | 10/1989 |
| 2006/0106649 A1 | 5/2006 | Eggers et al. | EP | 0 362 822 A2 | 4/1990 |
| 2006/0116639 A1 | 6/2006 | Russell | EP | 0 364 010 A2 | 4/1990 |
| 2006/0122867 A1 | 6/2006 | Eggers et al. | EP | 362822 | 4/1990 |
| 2006/0129429 A1 | 6/2006 | Moubayed et al. | EP | 0 396 003 A2 | 11/1990 |
| 2006/0132283 A1 | 6/2006 | Eberhart et al. | EP | 399119 | 11/1990 |
| 2006/0136271 A1 | 6/2006 | Eggers et al. | EP | 0 416 910 | 3/1991 |
| 2006/0143051 A1 | 6/2006 | Eggers et al. | EP | 0 416 911 | 3/1991 |
| 2006/0184121 A1 | 8/2006 | Brockman et al. | EP | 0 416 912 | 3/1991 |
| 2006/0184123 A1 | 8/2006 | Gillespie, Jr. et al. | EP | 0 419 094 | 3/1991 |
| 2006/0184154 A1 | 8/2006 | Moberg et al. | EP | 0 431 310 | 6/1991 |
| 2006/0189923 A1 | 8/2006 | Neftel et al. | EP | 0 446 605 | 9/1991 |
| 2006/0190302 A1 | 8/2006 | Eggers et al. | EP | 0 453 211 | 10/1991 |
| 2006/0200369 A1 | 9/2006 | Batch et al. | EP | 0 468 603 | 1/1992 |
| 2006/0202859 A1 | 9/2006 | Mastrototaro et al. | EP | 0 495 538 A2 | 7/1992 |
| 2006/0219644 A1 | 10/2006 | O'Hara et al. | EP | 0 496 436 A2 | 7/1992 |
| 2006/0229551 A1 | 10/2006 | Martinez | EP | 0 497 041 | 8/1992 |
| 2006/0243804 A1 | 11/2006 | Christoffersen et al. | EP | 0 499 903 | 8/1992 |
| 2006/0258985 A1 | 11/2006 | Russell | EP | 0 503 670 | 9/1992 |
| 2006/0271020 A1 | 11/2006 | Huang et al. | EP | 0 508 556 A1 | 10/1992 |
| 2006/0287884 A1 | 12/2006 | Sandy et al. | EP | 0 524 605 | 1/1993 |
| 2006/0287887 A1 | 12/2006 | Hutchinson et al. | EP | 0 544 393 | 6/1993 |
| 2007/0048161 A1 | 3/2007 | Moubayed | EP | 0 554 716 | 8/1993 |
| 2007/0058412 A1 | 3/2007 | Wang et al. | EP | 690961 | 1/1995 |
| 2007/0060871 A1 | 3/2007 | Istoc et al. | EP | 0 648 509 | 4/1995 |
| 2007/0073228 A1 | 3/2007 | Mernoe et al. | EP | 0646382 | 4/1995 |
| 2007/0073235 A1 | 3/2007 | Estes et al. | EP | 0646383 | 4/1995 |
| 2007/0073236 A1 | 3/2007 | Mernoe et al. | EP | 0 681 847 | 11/1995 |
| 2007/0077152 A1 | 4/2007 | Knauper et al. | EP | 0 731 275 | 9/1996 |
| 2007/0078370 A1 | 4/2007 | Shener et al. | EP | 0 891 784 | 1/1999 |
| 2007/0078431 A1 | 4/2007 | Hudson et al. | EP | 0 893 131 | 1/1999 |
| 2007/0083153 A1 | 4/2007 | Haar | EP | 0 893 132 | 1/1999 |
| 2007/0083292 A1 | 4/2007 | Knauper et al. | EP | 0 898 981 | 3/1999 |
| 2007/0088249 A1 | 4/2007 | Duffy et al. | EP | 0 899 564 | 3/1999 |
| 2007/0088269 A1 | 4/2007 | Valego et al. | EP | 0 919 250 | 6/1999 |
| 2007/0100316 A1 | 5/2007 | Traxinger | EP | 0 931 555 | 7/1999 |
| 2007/0104599 A1 | 5/2007 | Michels et al. | EP | 0 934 752 | 8/1999 |
| 2007/0106218 A1 | 5/2007 | Yodfat et al. | EP | 0 985 420 | 3/2000 |
| 2007/0107490 A1 | 5/2007 | Artsyukhovich et al. | EP | 0 985 421 | 3/2000 |
| 2007/0118405 A1 | 5/2007 | Campbell et al. | EP | 0 988 867 | 3/2000 |
| 2007/0148010 A1 | 6/2007 | Michels et al. | EP | 1 045 146 | 10/2000 |
| 2007/0156033 A1 | 7/2007 | Causey, III et al. | EP | 1 101 503 | 5/2001 |
| 2007/0156092 A1 | 7/2007 | Estes et al. | EP | 1 101 504 | 5/2001 |
| 2007/0167905 A1 | 7/2007 | Estes et al. | EP | 1108891 | 6/2001 |
| 2007/0167912 A1 | 7/2007 | Causey et al. | EP | 1225445 | 7/2002 |
| 2007/0173762 A1 | 7/2007 | Estes et al. | EP | 1 251 276 | 10/2002 |
| 2007/0179444 A1 | 8/2007 | Causey et al. | EP | 1 357 372 | 10/2003 |
| 2007/0183913 A1 | 8/2007 | Voyeux | EP | 1 391 215 | 2/2004 |
| 2007/0212240 A1 | 9/2007 | Voyeux et al. | EP | 1 400 691 | 3/2004 |
| 2007/0217932 A1 | 9/2007 | Voyeux et al. | EP | 1393762 | 3/2004 |
| 2008/0015507 A1 | 1/2008 | Cartledge et al. | EP | 1 501 037 | 1/2005 |
| 2008/0045902 A1 | 2/2008 | Estes et al. | EP | 1 532 995 | 5/2005 |
| 2008/0045903 A1 | 2/2008 | Estes et al. | EP | 1 535 637 | 6/2005 |
| 2008/0045904 A1 | 2/2008 | Estes et al. | EP | 1 537 886 | 6/2005 |
| 2008/0045931 A1 | 2/2008 | Estes et al. | EP | 1 563 859 | 8/2005 |
| | | | EP | 1576971 | 9/2005 |
| FOREIGN PATENT DOCUMENTS | | | EP | 1 609 500 | 12/2005 |
| DE | 41 04814 | 3/1991 | EP | 1 612 423 | 1/2006 |
| DE | 4037797 | 2/1992 | EP | 1612424 | 1/2006 |
| DE | 4307758 | 9/1994 | EP | 1616588 | 1/2006 |
| DE | 19525926 | 11/1996 | EP | 1 642 608 | 4/2006 |
| DE | 29806966 U1 | 9/1998 | EP | 1 739 585 | 1/2007 |
| DE | 19738146 | 3/1999 | EP | 1 762 263 | 3/2007 |
| DE | 20000965 U1 | 4/2000 | EP | 1 769 812 | 4/2007 |
| DE | 199 16 876 | 11/2000 | EP | 1 769 813 | 4/2007 |
| DE | 10020496 | 11/2000 | EP | 1 769 815 | 4/2007 |
| DE | 199 60 668 | 8/2001 | EP | 1 770 573 | 4/2007 |
| DE | 10022022 | 11/2001 | EP | 1772162 | 4/2007 |
| DE | 201 01 082 | 7/2002 | ES | 2238897 | 9/2005 |
| DE | 202 06 474 | 10/2003 | FR | 2 690 622 | 11/1993 |

| | | | | | | |
|---|---|---|---|---|---|---|
| FR | 2792840 | 11/2000 | | WO | WO 00/16823 | 3/2000 |
| GB | 1578022 | 10/1980 | | WO | WO 00/18449 | 4/2000 |
| GB | 2109474 | 6/1983 | | WO | WO 00/21587 | 4/2000 |
| GB | 2285837 A | 7/1995 | | WO | WO 00/48112 | 8/2000 |
| GB | 2309801 A | 8/1997 | | WO | WO 00/51671 | 9/2000 |
| GB | 2312022 | 10/1997 | | WO | WO 00/57941 | 10/2000 |
| GB | 2312046 | 10/1997 | | WO | WO 00/66203 | 11/2000 |
| GB | 2312055 | 10/1997 | | WO | WO 00/72181 | 11/2000 |
| GB | 2338752 | 12/1999 | | WO | WO 01/23277 | 4/2001 |
| GB | 2338753 | 12/1999 | | WO | WO 01/34222 | 5/2001 |
| GB | 2338754 | 12/1999 | | WO | WO 01/39816 | 6/2001 |
| GB | 2338755 | 12/1999 | | WO | WO 01/54566 | 8/2001 |
| GB | 2338756 | 12/1999 | | WO | WO 01/97113 | 12/2001 |
| GB | 2338757 | 12/1999 | | WO | WO 02/11049 | 2/2002 |
| GB | 2338758 | 12/1999 | | WO | WO 02/36044 | 5/2002 |
| GB | 2338759 | 12/1999 | | WO | WO 02/38204 | 5/2002 |
| GB | 2338760 | 12/1999 | | WO | WO 02/43573 | 6/2002 |
| GB | 2338992 | 1/2000 | | WO | WO 02/49259 | 6/2002 |
| GB | 2342188 | 4/2000 | | WO | WO 02/055137 | 7/2002 |
| GB | 2342189 | 4/2000 | | WO | WO 02/061281 | 8/2002 |
| GB | 2417052 | 2/2006 | | WO | WO 02/066101 | 8/2002 |
| JP | 9220279 | 8/1997 | | WO | WO 02/069099 | 9/2002 |
| JP | 07308379 | 4/1998 | | WO | WO 02/081919 | 10/2002 |
| JP | 2001218841 | 8/2001 | | WO | WO03/011377 | 2/2003 |
| JP | 06205829 | 11/2001 | | WO | WO03/024385 | 3/2003 |
| JP | 2004000498 | 1/2004 | | WO | WO 03/053503 | 7/2003 |
| JP | 2004162647 | 6/2004 | | WO | WO 03/105930 | 12/2003 |
| JP | 2005095577 | 4/2005 | | WO | WO 03/105931 | 12/2003 |
| JP | 2006034719 | 2/2006 | | WO | WO 03/105932 | 12/2003 |
| JP | 3124022 | 7/2006 | | WO | WO 2004/012043 | 2/2004 |
| KR | 10-0516727 | 9/2005 | | WO | WO 2004/024053 | 3/2004 |
| KR | 10-0553384 | 2/2006 | | WO | WO 2004/024214 | 3/2004 |
| KR | 10-0561243 | 3/2006 | | WO | WO 2004/033024 | 4/2004 |
| KR | 10-0607128 | 7/2006 | | WO | WO 2004/047641 | 6/2004 |
| KR | 10-0755528 | 8/2007 | | WO | WO 2004/087241 | 10/2004 |
| WO | WO 91/00113 | 1/1991 | | WO | WO 2004/093648 | 11/2004 |
| WO | WO 91/04759 | 4/1991 | | WO | WO 2004/095379 | 11/2004 |
| WO | WO 91/12848 | 9/1991 | | WO | WO 2004/111782 | 12/2004 |
| WO | WO 92/15349 | 9/1992 | | WO | WO 2005/032449 | 4/2005 |
| WO | WO 92/18175 | 10/1992 | | WO | WO 2005/050497 | 6/2005 |
| WO | WO 93/21978 | 11/1993 | | WO | WO 2005/056083 | 6/2005 |
| WO | WO 93/24893 | 12/1993 | | WO | WO 2005/061028 | 7/2005 |
| WO | WO 93/25816 | 12/1993 | | WO | WO 2005/062751 | 7/2005 |
| WO | WO 94/08647 | 4/1994 | | WO | WO 2005/088130 | 9/2005 |
| WO | WO 95/06817 | 3/1995 | | WO | WO 2005/089263 | 9/2005 |
| WO | WO 9517600 | 5/1995 | | WO | WO 2005/089835 | 9/2005 |
| WO | WO 95/17913 | 7/1995 | | WO | WO 2005/102417 | 11/2005 |
| WO | WO 95/24229 | 9/1995 | | WO | WO 2005/105182 | 11/2005 |
| WO | WO 96/01371 | 1/1996 | | WO | WO 2005/106251 | 11/2005 |
| WO | WO 96/03168 | 2/1996 | | WO | WO 2005/118027 | 12/2005 |
| WO | WO 96/08278 | 3/1996 | | WO | WO 2005/118054 | 12/2005 |
| WO | WO 96/08717 | 3/1996 | | WO | WO 2006/008364 | 1/2006 |
| WO | WO 96/20745 | 7/1996 | | WO | WO 2006/008376 | 1/2006 |
| WO | WO 96/20746 | 7/1996 | | WO | WO 2006/014200 | 2/2006 |
| WO | WO 96/27402 | 9/1996 | | WO | WO 2006/016122 | 2/2006 |
| WO | WO 96/28209 | 9/1996 | | WO | WO 2006/029237 | 3/2006 |
| WO | WO 96/34648 | 11/1996 | | WO | WO 2006/046242 | 5/2006 |
| WO | WO 96/36389 | 11/1996 | | WO | WO 2006/084464 | 8/2006 |
| WO | WO 97/02059 | 1/1997 | | WO | WO 2006/086701 | 8/2006 |
| WO | WO 97/07843 | 3/1997 | | WO | WO 2006/086723 | 8/2006 |
| WO | WO 97/21456 | 6/1997 | | WO | WO 2006/086735 | 8/2006 |
| WO | WO 97/32129 | 9/1997 | | WO | WO 2006/103711 | 10/2006 |
| WO | WO 97/37703 | 10/1997 | | WO | WO 2006/103712 | 10/2006 |
| WO | WO 97/37704 | 10/1997 | | WO | WO 2006/124202 | 11/2006 |
| WO | WO 97/37706 | 10/1997 | | WO | WO 2006/127905 | 11/2006 |
| WO | WO 98/13080 | 4/1998 | | WO | WO 2007/023329 | 3/2007 |
| WO | WO 98/14234 | 4/1998 | | WO | WO 2007/025268 | 3/2007 |
| WO | WO 98/20918 | 5/1998 | | WO | WO 2007/033010 | 3/2007 |
| WO | WO 98/56450 | 12/1998 | | WO | WO 2007/038059 | 4/2007 |
| WO | WO 98/56451 | 12/1998 | | WO | WO 2007/038060 | 4/2007 |
| WO | WO 98/56453 | 12/1998 | | WO | WO 2007/038091 | 4/2007 |
| WO | WO 99/10029 | 3/1999 | | WO | WO 2007/052277 | 5/2007 |
| WO | WO 99/22783 | 5/1999 | | WO | WO 2007/061368 | 5/2007 |
| WO | WO 99/47812 | 9/1999 | | WO | WO 2007/041843 | 4/2008 |
| WO | WO 99/64091 | 12/1999 | | WO | WO2008/082091 | 7/2008 |
| WO | WO 99/64093 | 12/1999 | | | | |
| WO | WO00/10628 | 3/2000 | | * cited by examiner | | |

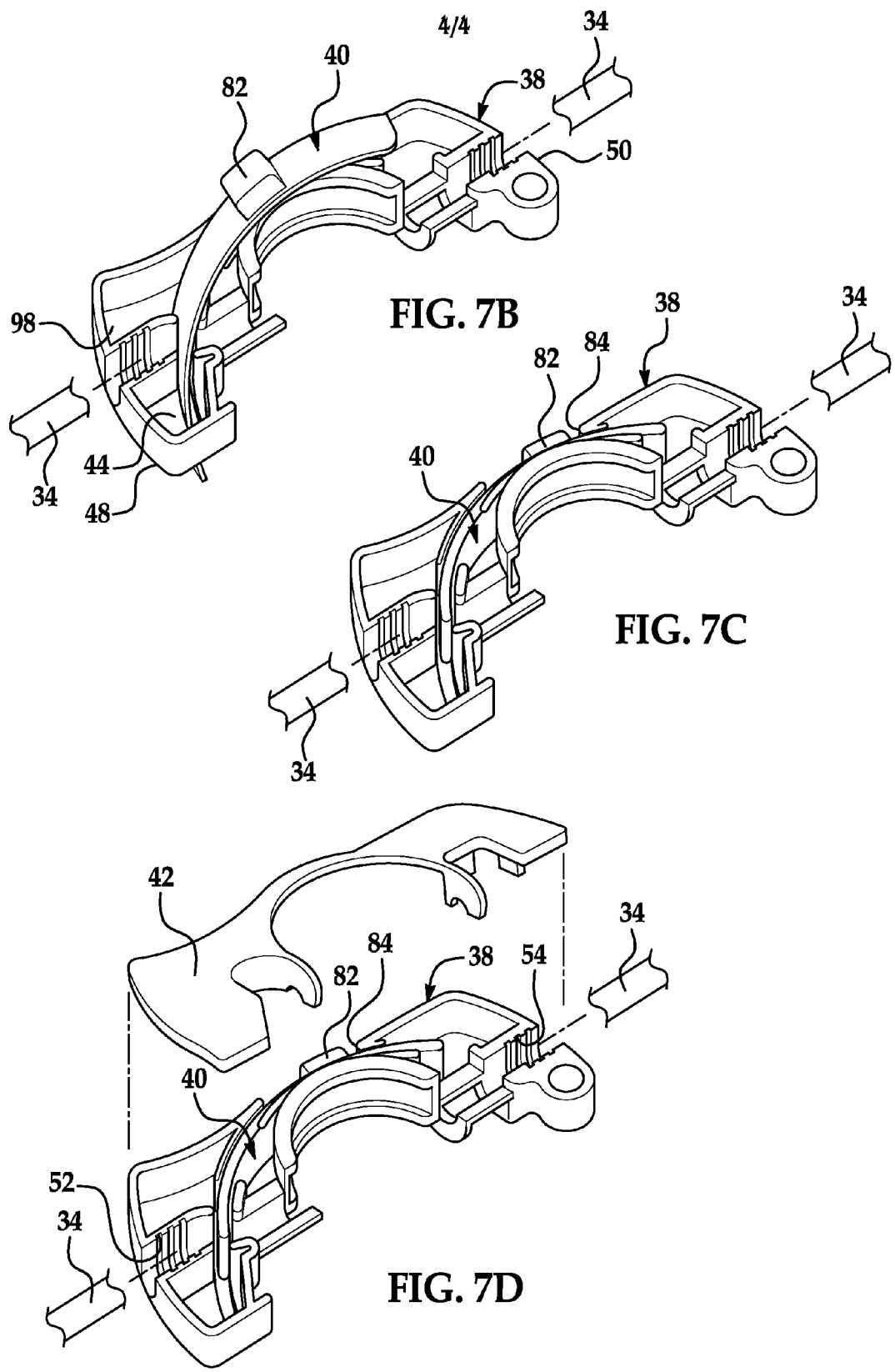

PERISTALTIC PUMP AND REMOVABLE CASSETTE THEREFOR

BACKGROUND

The present invention relates generally to a peristaltic pump and a removable cassette therefor.

Peristaltic pumps are often used to deliver fluid in a very controlled manner such as, for example, the intravenous delivery of medicine to a patient. The peristaltic pump may generally include a pump body having a cassette removably attached thereto, and a tube supported by the cassette. A fluid (e.g., medicine) flows through the tube, generally by increments, as the tube is occluded against a race formed in the cassette in response to rotational movement of a planetary system of rollers driven by a motorized drive shaft. In some instances, the cassette may further include an occlusion mechanism or occluder that interacts with the tube to occlude the tube to substantially prevent fluid inside the tube from flowing through the tube.

SUMMARY

A removable cassette for a peristaltic pump includes a cassette body and an occluder disposed at least partially in the cassette body and configured to be movable between an occluding position and a non-occluding position. The occluder includes an occluder body and an anti-ejection member integrally formed on the occluder body. The anti-ejection member is configured to substantially prevent the removal of the cassette from the peristaltic pump when the occluder is in the non-occluding position.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

FIG. 5A depicts the occluder in a non-occluding position, and FIG. 5B depicts the occluder in an occluding position;

FIGS. 7A-7D are perspective views of the removable cassette depicting steps of a method of assembling the removable cassette.

DETAILED DESCRIPTION

Embodiment(s) of the removable cassette for a peristaltic pump, as disclosed herein, advantageously include an occluder movable between an occluding position and a non-occluding position, where the occluder includes an anti-ejection member that substantially prevents removal of the removable cassette from the peristaltic pump when the occluder is in the non-occluding position. The occluder is relatively simple in design and generally does not include overly delicate and/or intricate parts that may be jammed or easily broken during operation and/or routine maintenance of the cassette. The peristaltic pump including the cassette also may advantageously provide feedback to a user thereby indicating to the user that the occluder is in the occluding position so that the cassette may be ejected from the pump. Further, the peristaltic pump including the cassette is relatively easy to assemble and to use.

As defined herein, the term "occlusion point" refers to an area or region on a tube at which the tube may be occluded by the occluder.

As also defined herein, the term "occluding position" refers to the position of the occluder in the cassette where the tube supported by the cassette is occluded at the occlusion point, thereby substantially preventing fluid from flowing through the tube at the occlusion point. The term "non-occluding position" refers to the position of the occluder in the cassette where the tube supported by the cassette is not occluded at the occlusion point, thereby allowing fluid to flow through the tube at the occlusion point.

As further defined herein, the term "ejection position" refers to the position of an anti-ejection member formed on the occluder where the anti-ejection member does not interface with a pump body retaining feature formed on the cassette body, thereby allowing the cassette to be removed from the pump body. The term "anti-ejection position" refers to the position of the anti-ejection member where the anti-ejection member interfaces with the pump body retaining feature, thereby preventing the cassette from being removed from the pump body.

Figure 1:
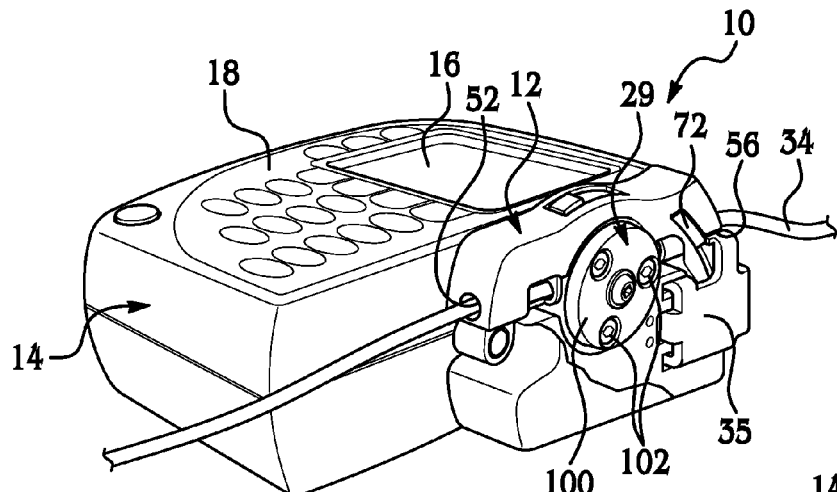
FIG. 1 is a perspective view of an embodiment of a peristaltic pump assembly including a pump body and a removable cassette assembled therewith.
Figure 2:
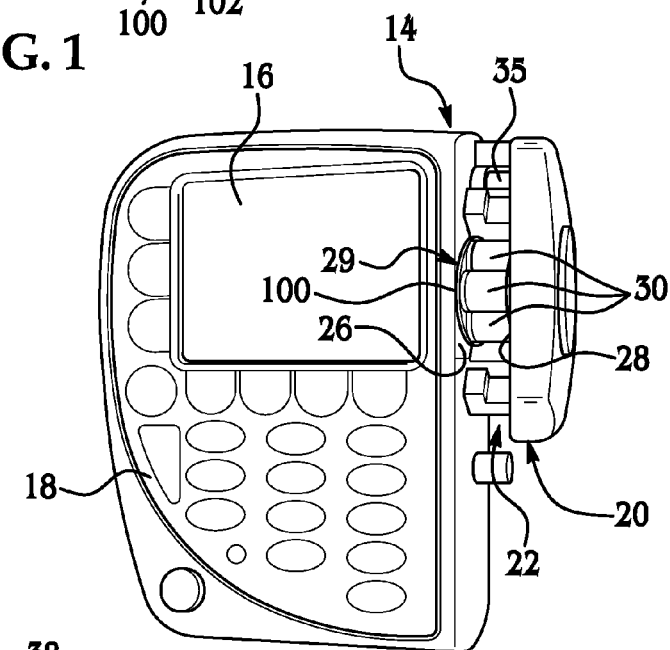
FIG. 2 is a perspective, plan view of the pump body shown in FIG. 1.

Referring now to FIGS. 1 and 2, together, a peristaltic pump assembly is generally depicted at 10. Pump assembly 10 includes a removable and disposable cassette 12 assembled with a pump body 14. The pump body 14 includes a display 16 that corresponds with a keypad 18 for inputting user information such as, for example, patient identification number, drug identification number, operator identification number, or the like. The display 16 also provides visual feedback to the operator or user of the pump 10 regarding, for example, the amount of medication administered to the patient, the flow rate of the medication, and the time for medication administration.

The pump body 14 also includes a cassette receiving portion 20 formed adjacent to the display 16. The cassette receiving portion 20 includes a partial cavity 22 defined by a floor (not shown) and two opposed walls 26, 28. A roller mechanism 29, including an assembly of satellite rollers 30 arranged in a planetary configuration, is housed within the cavity 22. The roller mechanism 29 is attached to a pump motor (not shown) through a bore (not shown) formed through the first opposed wall 26. In a non-limiting example, each roller 30 is slip-fit onto a respective pin (the backs of which are shown at 102 in FIG. 1) supported by a yoke 100 (shown in FIGS. 1 and 2). The yoke 100 is mounted to a drive shaft (not shown), which is operated by the pump motor. As the yoke rotates, the rollers 30 rotate as an assembly. It is to be understood that, since the rollers 30 are slip-fit onto the pins, the rollers 30 are also free to rotate individually in response to rotational forces imparted thereto from the rotational movement of the drive shaft. Details of an example of the pump body 14 including an example of the roller mechanism 29 may also be found in U.S.

application Ser. Nos. 11/862,302 and 11/862,326 filed concurrently herewith, which are commonly owned by the Assignee of the present disclosure, and are incorporated herein by reference in their entirety.

As shown in FIG. 1, a flexible tube 34, which is also disposable, is disposed in the cassette 12. In response to rotational movement of the rollers 30, portions of the flexible tube 34 that are in contact with the rollers 30 compress or are otherwise occluded against a race 36 (shown in FIG. 3) of the cassette 12. As a result, fluid is temporarily retained in the tube 34 between the occluded points. In this manner, fluid is urged through the tube via peristaltic wave action. The design of the cassette 12 will be described further in conjunction with FIGS. 3 and 4 below.

In a non-limiting example, the tube 34 may be classified as substantially flexible so that the tube may be compressed and/or occluded by the rollers 30. In an embodiment, the tube 34 is made of a polymeric material. Non-limiting examples of suitable polymeric materials include silicones, AUTOPRENE (an opaque thermoplastic rubber with high wear resistance derived from SANTOPRENE, commercially available from Advanced Elastomer Systems, a subsidiary of ExxonMobil Chemical located in Houston, Tex.), VITON (a black fluoroelastomer with resistance to concentrated acids, solvents, ozone, radiation and temperatures up to 200° C. with good chemical compatibility, commercially available from DuPont Performance Elastomers located in Wilmington, Del.), TYGON (good chemical resistance with a clear finish, commercially available from Saint-Gobain Performance Plastics Corporation located in Akron, Ohio), PROTHANE II (a transparent, blue, polyester, polyurethane tubing with good chemical resistance, commercially available from Randolph Austin Company located in Manchaca, Tex.), and/or the like, and/or combinations thereof. The inner diameter of the tube 34 may be selected based on the desirable flow rates and the desirable viscosities of the fluid that will flow therethrough.

A pump body retaining feature 35 (shown in FIG. 2) is located in the cassette receiving portion 20 of the pump body 14. The pump body retaining feature 35 is configured to matingly engage a cassette retaining feature 56 (shown in FIGS. 1 and 4) formed on the cassette 12. When the attaching mechanism 35 and coupling member 56 are engaged, the cassette 12 is secured to the pump body 14. In a non-limiting example, the pump body retaining feature 35 may be a clip movable between a closed position and an opened position. The closed position refers to the position of the pump body retaining feature 35 where the pump body retaining feature 35 engages the cassette retaining feature 56. The opened position refers to the position of the pump body retaining feature 35 when the pump body retaining feature 35 is moved away from the closed position.

Figure 3:
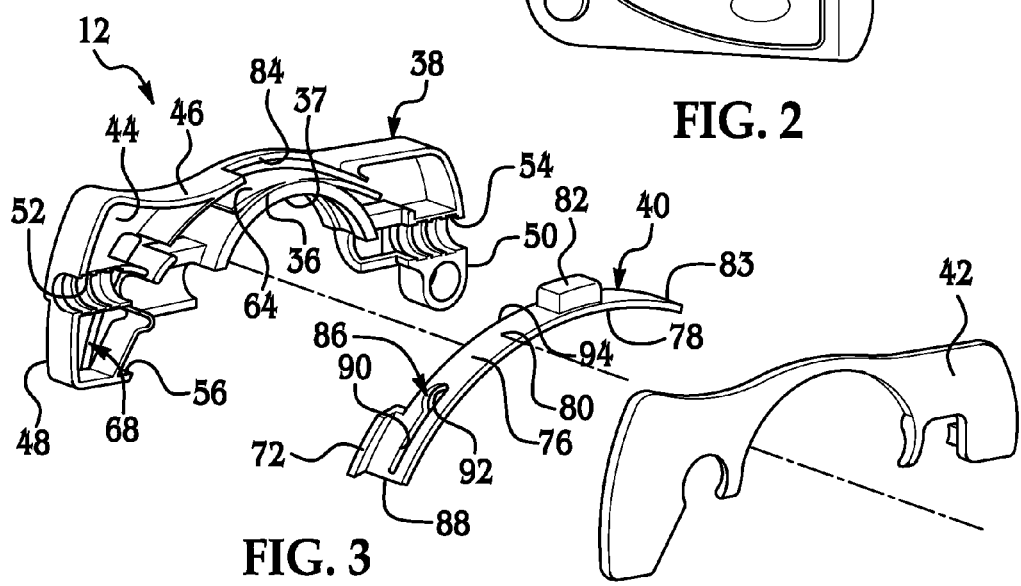
FIG. 3 is an enlarged, exploded perspective view of the removable cassette of FIG. 1, including a cassette body, an occluder, and a cassette cover.
Figure 4:
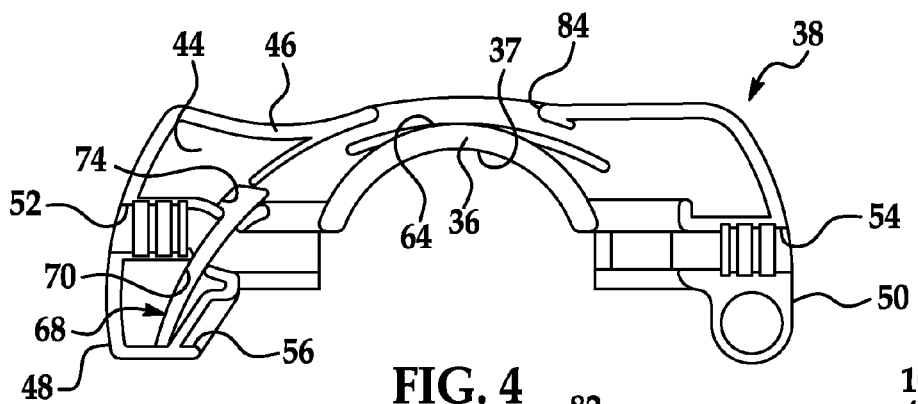
FIG. 4 is a plan view of the cassette body of FIG. 3.

With reference to FIGS. 3 and 4, the removable cassette 12 generally includes a cassette body 38, a removable occluder 40 at least partially disposed therein, and a cover 42 disposed over the cassette body 38. The cover 42 substantially secures the removable occluder 40 in the cassette body 38 when the occluder is assembled therewith.

Figure 5A:
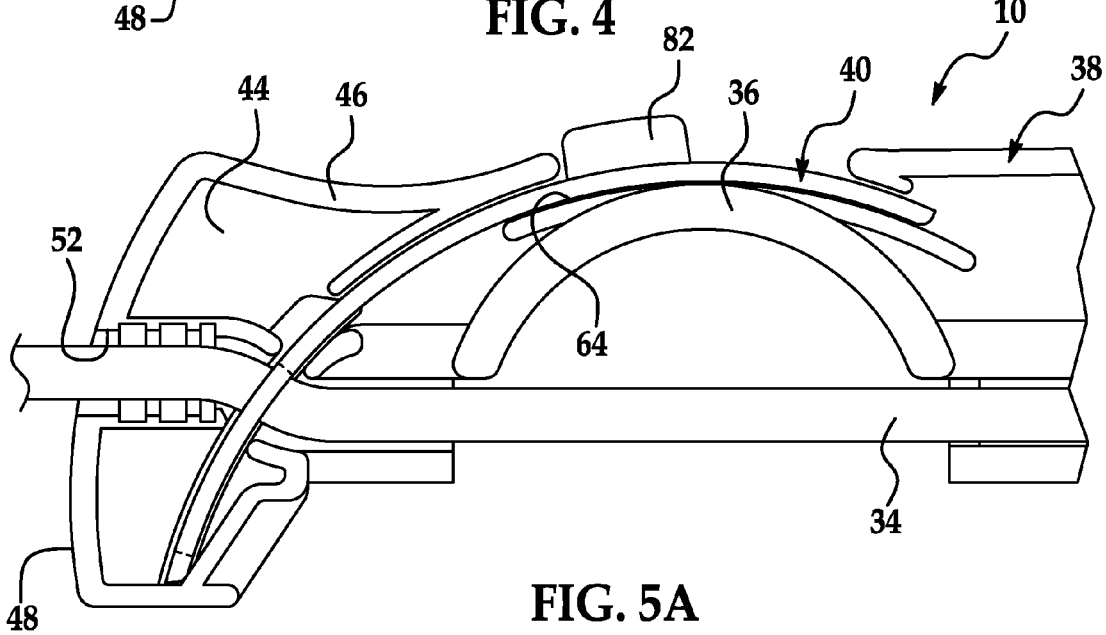
FIGS. 5A and 5B are enlarged, cut-away, plan views of the assembly of a flexible tube with the cassette body and the occluder of the removable cassette, where
Figure 5B:
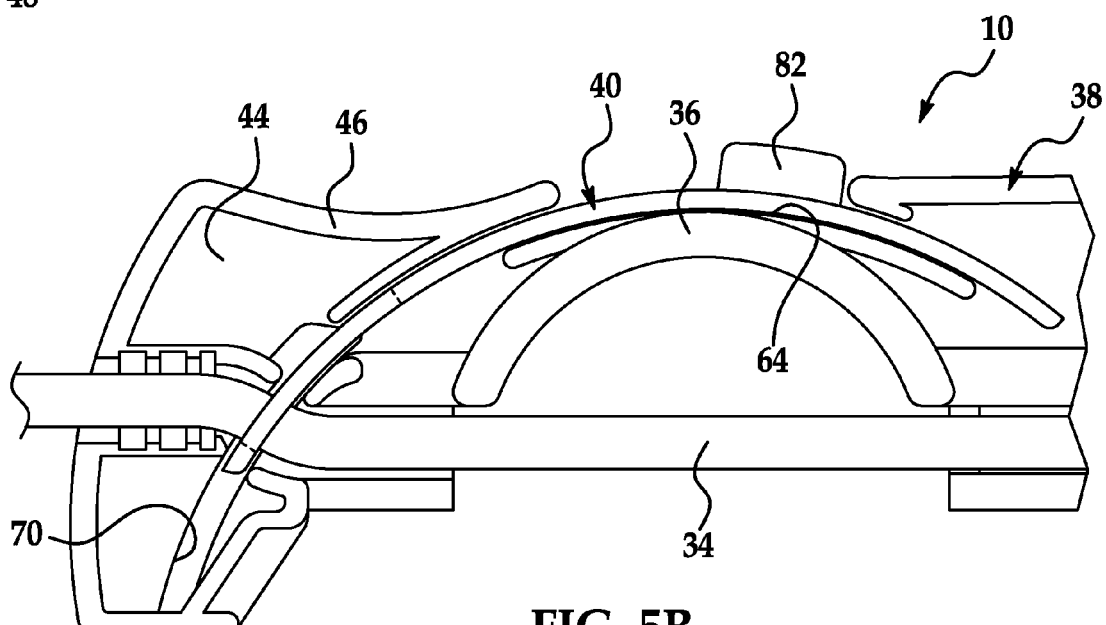

The cassette body 38 is a single, integrally formed piece of polymeric material and may be fabricated using, for example, injection molding, cast molding, and/or the like. The cassette body 38 includes a base 44 having a wall 46 substantially normal to the base 44 and surrounding at least a portion of the perimeter of the base 44. The cassette body 38 further includes two opposed ends 48, 50. An inlet 52 is formed at the first end 48 and is configured to receive a first end of the tube 34. An outlet 54 is formed in the cassette body 38 at the second end 50, where the outlet 54 is configured to receive a second end of the tube 34. An assembly of the tube 34 with the cassette body 38 is shown in FIGS. 5A and 5B.

With reference to FIGS. 3-5B, the race 36 is integrally formed in the cassette body 38 and is positioned substantially normal to the base 44 and projects outwardly therefrom. The race 36 includes an occlusion surface 37 for the tube 34 to occlude the tube 34 when the rollers 30 force the tube 34 against the occlusion surface 37 during operation of the pump 10. Formed on the other side of the race 36 is a slide surface 64, which is a substantially smooth surface for slidable movement of the occluder 40 when the occluder 40 is assembled with the cassette body 38. The assembly of the occluder 40 with the cassette body 38 will be described in more detail below in conjunction with FIGS. 7A-7D.

Cassette retaining feature 56 (shown in FIGS. 3 and 4) is disposed adjacent to the inlet 52 formed in the cassette body 38. As mentioned above, the cassette retaining feature 56 is matingly engageable with the pump body retaining feature 35 included with the pump body 14 (shown in FIG. 2). Generally, the cassette retaining feature 56 is designed to complement or otherwise mate with the pump body retaining feature 35. In a non-limiting example, the cassette retaining feature 56 is a ledge formed in the cassette body 38 and is configured to receive and hold the pump body retaining feature 35 (e.g., a clip) when the pump body retaining feature 35 engages the cassette retaining feature 56. In use, when the cassette 12 is assembled with the pump body 14, the pump body retaining feature 35 captures the cassette retaining feature 56 and releasably attaches the cassette 12 to the pump body 14. It is within the purview of the present disclosure that other configurations or designs for the pump body retaining feature 35 and the cassette retaining feature 56 may also be used to removably attach the cassette 12 to the pump body 14, as desired.

The cassette body 38 also includes an anti-ejection member-receiving slot 68 formed therein. As shown in FIG. 4, the anti-ejection member-receiving slot 68 may generally resemble a key hole slot, where the slot 68 includes a narrow portion 70 and a wider portion 74. It is to be understood that the key hole configuration of the slot 68 facilitates assembly of the occluder 40 with the cassette body 38. This assembly will be described in more detail below. It is further to be understood that anti-ejection member-receiving slot 68 is configured to receive an anti-ejection member 72 (shown in FIG. 2) formed on the occluder 40, and further operates as a guide for the anti-ejection member 72. More specifically, the slot 68 is configured to allow the anti-ejection member 72 to move into a position to substantially prevent removal of the cassette 12 when the occluder 40 is in the non-occluding position; or to move into a position to allow removal of the cassette 12 when the occluder 40 is in the occluding position. Movement of the anti-ejection member 72 will be described further in conjunction with FIGS. 6A and 6B.

As shown in FIG. 3, the occluder 40 generally includes an occluder body 76 and the anti-ejection member 72 integrally formed thereon, and is configured to be movable between the occluding position and the non-occluding position. In an embodiment, the occluder body 76 is convex in shape and substantially conforms to the shape of the slide surface 64 formed adjacent to the race 36. It is to be understood that other shapes (e.g., a flat shape) may also be used for the occluder body 76 as long as the cassette body 38 is formed to accommodate the shape of the occluder body 76.

The occluder 40 includes first and second opposed sides 78, 80, where the first side 78 is configured to slidably contact the slide member 64, and the second side 80 includes a toggle member 82 extending outwardly therefrom and located proximate to a first end 83 of the occluder 40. In an embodiment, the toggle member 82 is embossed or otherwise defined in the occluder body 76 such that the toggle member 82 protrudes from the second side 80. In this embodiment, when the occluder 40 is assembled with the cassette 12, the toggle member 82 extends outwardly from the occluder body 76 and through an opening 84 defined in the cassette body 38. In use, when the cassette 12 is assembled with the pump body 14, the toggle member 82 actuates movement of the occluder 40 between the non-occluding position and the occluding position, shown in FIGS. 5A and 5B, respectively. Further, when the user moves the toggle member 82 to allow the occluder 40 to move into the occluding position, the cassette 12 provides feedback to the user that the occluder 40 is in the occluding position. Non-limiting examples of feedback include tactile feedback, audible feedback, and/or the like, and/or combinations thereof. In a non-limiting example, a releasable locking feature, e.g., a detent, may be provided between the occluder 40 and the cassette body 38 that may audibly "click" and/or provide a feel to a user that the occluder 40 has been placed into the occluded position.

The occluder 40 also includes an occlusion slot 86 formed in the occluder body 76 proximate to a second end 88 of the occluder 40. The occlusion slot 86 is configured to substantially occlude the tube 34 when the occluder 40 is in the occluding position, and is further configured to substantially allow free flow of fluid through the tube 34 when the occluder is in the non-occluding position. In an embodiment, the occlusion slot 86 is a key hole slot having a narrow portion 90 and a wider portion 92. In this embodiment, and as shown in FIGS. 5A and 5B, the occlusion slot 86 receives the tube 34 in the wider portion 92 thereof when the occluder 40 is in the non-occluding position, and receives the tube 34 in the narrow portion 90 when the occluder 40 is in the occluding position.

Figure 6A:
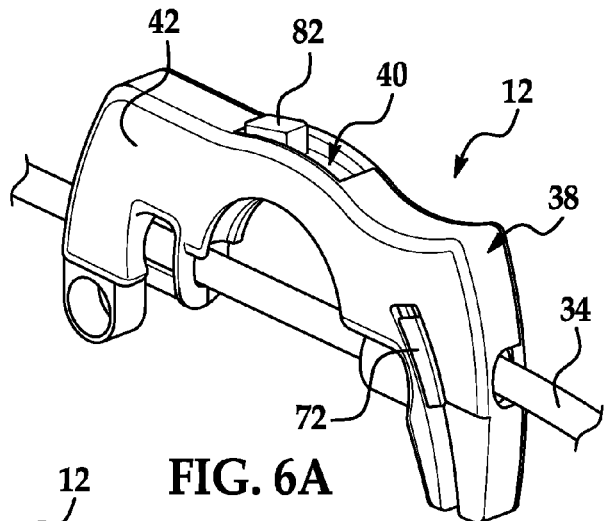
FIGS. 6A and 6B are perspective views of the removable cassette showing the position of an anti-ejection feature of the occluder when the occluder is in the occluding and the non-occluding positions, respectively.
Figure 6B:
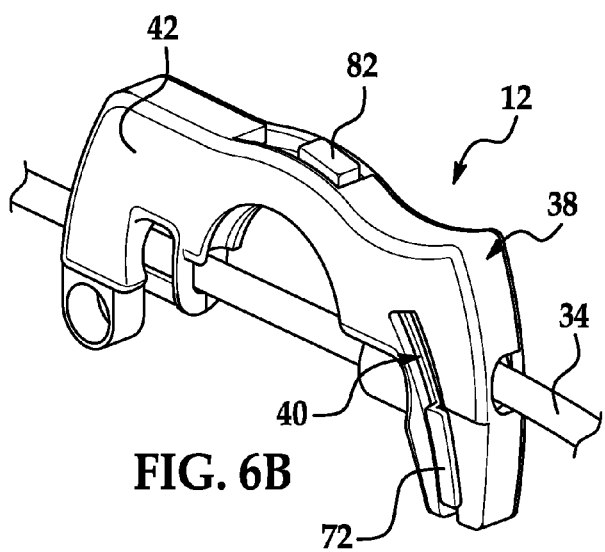

With reference again to FIG. 3, the occluder 40 further includes the anti-ejection member 72 formed on an edge 94 of the occluder body 76 located proximate to the second end 88. The anti-ejection member 72 is generally a tab projecting from the edge 94 and extending substantially perpendicular thereto. The anti-ejection member 72 is configured to substantially prevent removal of the cassette 12 from the peristaltic pump 10 when the occluder 40 is in the non-occluding position, and is further configured to allow removal of the cassette 12 from the peristaltic pump 10 when the occluder 40 is in the occluding position. This may be accomplished by causing the anti-ejection member 72 to either lock or unlock the cassette retaining feature 56. In a non-limiting example, as shown in FIG. 6A, when the occluder 40 is in the occluding position, the anti-ejection member 72 moves into an ejection position. In this position, the anti-ejection member 72 does not interface with the pump body retaining feature 35, thereby allowing the cassette 12 to be removed from the pump 10. In another non-limiting example, as shown in FIG. 6B, when the occluder 40 is in the non-occluding position, the anti-ejection member 72 is in an anti-ejection position. In this position, the anti-ejection member 72 interfaces with the pump body retaining feature 35, thereby substantially locking the cassette 12 to the pump body 14. This prevents the cassette 12 from being removed or ejected from the pump 10.

A method of assembling the cassette 12 is shown in FIGS. 7A-7D. The method generally includes providing the cassette body 38 and providing the occluder 40 as described above, and at least partially disposing the occluder 40 in the cassette body 38. An embodiment of a method of disposing the occluder 40 in the cassette body 38 may be accomplished as set forth below.

Figure 7A:
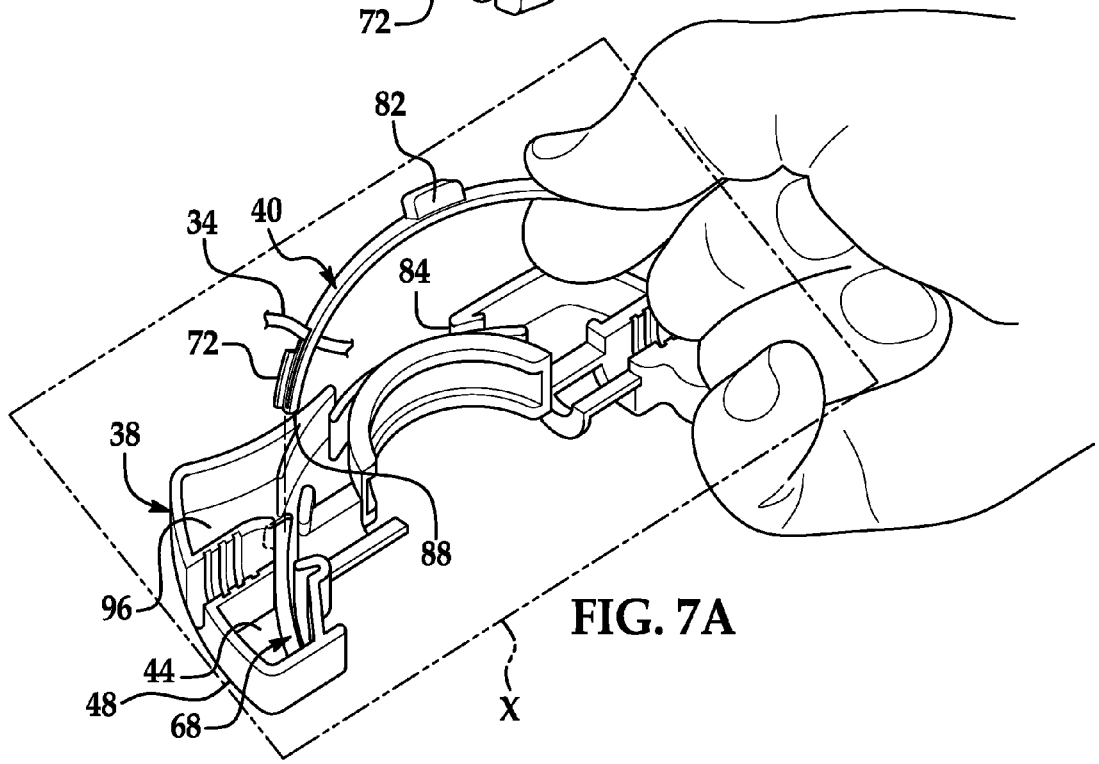

Referring now to FIG. 7A, the occluder 40, including the tube 34 (which is schematically depicted in FIG. 7A) disposed or otherwise threaded through the slot 86, is positioned substantially perpendicular to a plane X parallel to the cassette body 38 (e.g., plane X includes points defined by ends 48 and 50 (shown in FIG. 7B) of the cassette body 38). In more detail, the second end 88 of the occluder 40 including the anti-ejection member 72 is positioned substantially perpendicularly to the anti-ejection member-receiving slot 68 at a first side 96 of the base 44 of the cassette body 38. It is to be understood that the end 88 including the anti-ejection member 72 is substantially complementarily shaped with the anti-ejection member-receiving slot 68 so that the occluder 40 can easily slide therein. The positioning of the second end 88 is such that the anti-ejection member 72 is substantially aligned with the wide portion 92 of the slot 68.

Second, as shown in FIG. 7B, the occluder 40 is passed through the anti-ejection member-receiving slot 68 until the anti-ejection member 72 is exposed on a second, opposed side 98 of the base 44.

Third, and as shown in FIG. 7C, the occluder 40 is rotated counter-clockwise about 90° relative to the base 44 so that a side edge 94 (shown in FIG. 3) of the occluder body 76 is substantially aligned with the plane X. When the occluder 40 is rotated into the cassette body 38, the toggle member 82 is received through the opening 84 for access thereto by a user of the cassette 12.

Fourth, and as shown in FIG. 7D, the tube 34, already disposed through the slot 86 (best seen in FIG. 3) formed in the occluder 40, is fed through the inlet 52 formed in the cassette body 38 and through the outlet 54. The cover 42 is then disposed over the cassette body 38 and secured thereto via latching, snapping, welding, and/or the like, and/or combinations thereof. When the cover 42 is secured to the cassette body 38, the occluder 40 is substantially secured therein.

It is to be understood that the term "couple/coupled" or the like is broadly defined herein to encompass a variety of divergent coupling arrangements and assembly techniques. These arrangements and techniques include, but are not limited to (1) the direct coupling between one component and another component with no intervening components therebetween; and (2) the coupling of one component and another component with one or more components therebetween, provided that the one component being "coupled to" the other component is somehow operatively coupled to the other component (notwithstanding the presence of one or more additional components therebetween).

While several embodiments have been described in detail, it will be apparent to those skilled in the art that the disclosed embodiments may be modified. Therefore, the foregoing description is to be considered exemplary rather than limiting.

What is claimed is:

1. A removable cassette for a peristaltic pump, comprising:
   a cassette body including a convex slide surface; and
   an occluder disposed at least partially in the cassette body and configured to be movable along the convex slide surface between an occluding position and a non-occluding position, the occluder including:
   an occluder body having a concave inner side slidably engaging the convex slide surface of the cassette body; and
   an anti-ejection member integrally formed on the occluder body, wherein the anti-ejection member is configured to substantially prevent removal of the cassette from the peristaltic pump when the occluder is in the non-occluding position.

2. The removable cassette as defined in claim 1 wherein the anti-ejection member allows removal of the cassette from the peristaltic pump when the occluder is in the occluding position.

3. The removable cassette as defined in claim 2 wherein the cassette body includes an anti-ejection member-receiving slot formed therein.

4. The removable cassette as defined in claim 3, further comprising:
an opening defined in the cassette body; and
a toggle member extending outwardly from the occluder body and through the opening.

5. The removable cassette as defined in claim 4 wherein the toggle member actuates movement of the occluder between the occluding position and the non-occluding position.

6. The removable cassette as defined in claim 1, further comprising:
a tube operatively disposed in the cassette body; and
an occlusion slot defined in the occluder body, the occlusion slot being configured to substantially occlude the tube when the occluder is in the occluding position, and the occlusion slot being configured to substantially allow free flow through the tube when the occluder is in the non-occluding position.

7. The removable cassette as defined in claim 6 wherein the occlusion slot is a key hole slot.

8. The removable cassette as defined in claim 6 wherein the anti-ejection member is a tab integrally formed with a side edge of the occluder body and operatively receivable within an anti-ejection member-receiving slot formed in the cassette body.

9. The removable cassette as defined in claim 1, further comprising a cover disposed over the cassette body and substantially securing the occluder in the cassette body.

10. The removable cassette as defined in claim 1 wherein the removable cassette provides tactile feedback, audible feedback, or combinations thereof when the occluder is moved into the occluding position.

11. A peristaltic pump, comprising:
a pump body;
a cassette removably attached to the pump body, the cassette including a cassette body and an occluder;
the cassette body including a convex slide surface;
the occluder being disposed at least partially in the cassette body and configured to be movable along the convex slide surface between an occluding position and a non-occluding position, the occluder including:
an occluder body having a concave inner side slidably engaging the convex slide surface of the cassette body; and
an anti-ejection member integrally formed on the occluder body, wherein the anti-ejection member is configured to substantially prevent removal of the cassette from the peristaltic pump when the occluder is in the non-occluding position.

12. The peristaltic pump as defined in claim 11, wherein the pump body comprises a pump body retaining feature configured to releasably attach the cassette to the pump body; and wherein the cassette comprises a cassette retaining feature matingly engageable with the pump body retaining feature.

13. The peristaltic pump as defined in claim 12 wherein when the occluder is in the occluding position, the anti-ejection member unlocks the cassette retaining feature, thereby allowing the cassette to be removed from the peristaltic pump.

14. The peristaltic pump as defined in claim 12 wherein when the occluder is in the non-occluding position, the anti-ejection member substantially locks the cassette retaining feature, thereby preventing the cassette from being removed from the peristaltic pump.

15. The peristaltic pump as defined in claim 11 wherein the cassette provides tactile feedback, audible feedback, or combinations thereof when the occluder is moved into the occluding position.

16. A method of assembling a removable cassette for a peristaltic pump, comprising:
at least partially disposing an occluder in a cassette body, the occluder including an occluder body having an anti-ejection member integrally formed on a side edge thereof, and the cassette body including a flat base defining a plane, wherein the cassette body includes an anti-ejection member-receiving slot formed therein;
positioning the occluder substantially perpendicular to the plane and substantially aligning a portion of the occluder body including the anti-ejection member with the anti-ejection member-receiving slot;
sliding the anti-ejection member through the slot; and
rotating the occluder body so that the side edge is substantially parallel to the plane.

17. The method as defined in claim 16 wherein the portion of the occluder body is substantially complementarily shaped with the anti-ejection member-receiving slot.

18. The method as defined in claim 16 wherein the cassette body further includes an opening formed therein, and wherein the method further comprises receiving a toggle member through the opening, wherein the toggle member extends outwardly from the occluder body.

19. The method as defined in claim 16 wherein the occluder further includes an occlusion slot formed therein, and wherein prior to at least partially disposing the occluder in the cassette body, and the method further comprises disposing a tube in the cassette body and through the occlusion slot.

20. The method as defined in claim 19, further comprising disposing a cover over the cassette body, thereby substantially securing the occluder therein.

\* \* \* \* \*